(12) United States Patent
Liu

(10) Patent No.: US 9,259,438 B2
(45) Date of Patent: Feb. 16, 2016

(54) METHODS FOR IN VITRO MATURATION OF OVARIAN FOLLICLES

(76) Inventor: Kui Liu, Umea (SE)

(*) Notice: Subject to any disclaimer, the term of this patent is extended or adjusted under 35 U.S.C. 154(b) by 299 days.

(21) Appl. No.: 12/812,930

(22) PCT Filed: Jan. 19, 2009

(86) PCT No.: PCT/SE2009/050049
§ 371 (c)(1),
(2), (4) Date: Oct. 8, 2010

(87) PCT Pub. No.: WO2009/091332
PCT Pub. Date: Jul. 23, 2009

(65) Prior Publication Data
US 2011/0015169 A1    Jan. 20, 2011

Related U.S. Application Data

(60) Provisional application No. 61/021,639, filed on Jan. 17, 2008, provisional application No. 61/024,210, filed on Jan. 29, 2008.

(51) Int. Cl.
*A61K 35/54*    (2015.01)
*C12Q 1/42*    (2006.01)
*A61K 33/24*    (2006.01)
*G01N 33/50*    (2006.01)

(52) U.S. Cl.
CPC . *A61K 33/24* (2013.01); *C12Q 1/42* (2013.01); *G01N 33/502* (2013.01)

(58) Field of Classification Search
USPC ......................................................... 514/492
See application file for complete search history.

(56) References Cited

U.S. PATENT DOCUMENTS

| | | | |
|---|---|---|---|
| 6,737,272 B2 * | 5/2004 | Kuo et al. | 435/375 |
| 2007/0203098 A1 | 8/2007 | Garlich et al. | |
| 2007/0292532 A1 * | 12/2007 | Woscholski et al. | 424/646 |

FOREIGN PATENT DOCUMENTS

| | | |
|---|---|---|
| JP | 2007-532552 A | 11/2007 |
| WO | WO-2004075897 A1 | 9/2004 |
| WO | WO-2005019440 A1 | 3/2005 |
| WO | WO-2005097119 A2 | 10/2005 |
| WO | WO-2006007542 A1 | 1/2006 |

OTHER PUBLICATIONS

Kuo et al. U.S. Pat. No. 6,737,272 Hardy et al. Brit. Med. Bull. 2000, 56(3), 588-602.*
Stedman's Medical Dictionary, Lippincott, Willliam & Wilkins, http://www.stedmansonline.com/.*
Kwak et al. Molecular Neurodegen. 2010, 8 (49) 1-12.*
Makabe et al. Microscopy Res. and Tech., 2006, 69, 436-449.*
Froment et al. FEBS Lett. 2005, 579, 2376-2382.*
Wu et al., Neurosci. Lett., 2006, 404, 98-102.*
Cid et al., Oncogene, 2008, 27, 5431-5442.*
Chang, K. J., et al., "Differential Effects of Gonadotropin and Orthovanadate on Oocyte Maturation, Ovulation, and Prostaglandin Synthesis by Rana Ovarian Follicles In Vitro", *The Journal of Experimental Zoology*, 277, (1997), 155-165.
Fan, H.-Y., et al., "Targeted Disruption of Pten in Ovarian Granulosa Cells Enhances Ovulation and Extends the Life Span of Luteal Cells", *Molecular Endocrinology*, 22, (2008), 2128-2140.
Goetz, F. W., "Involvement of Protein Kinase C in Agonist-Stimulated Goldfish Ovulation", *Biology of Reproduction*, 48, (1993), 846-850.
Hainaut, P., et al., "Insulin-like effects of vanadate on glucose uptake and on maturation in Xenopus laevis oocytes", *Cell Regulation*, vol. 2, (Apr. 1991), 317-327.
Hsu, S.-Y., et al., "Oxoanions stimulate in vitro ovulation and signal transduction pathways in goldfish (*Carassius auratus*) follicles", *Am. J. Physiol.—Endocrinol. Metab.*, 263(5), (1992), B943-B949.
Hsu, S.-Y., et al., "Synergistic Induction of Ovulation and Prostaglandin Synthesis in Goldfish (*Carassius auratus*) Follicles by Sodium Orthovanadate and Hydrogen Peroxide", *Biology of Reproduction*, 45, (1991), 912-917.
Mailhes, J. B., et al., "Vanadate, an inhibitor of tyrosine phosphates, induced premature anaphase in oocytes and aneuploidy and polyploidy in mouse bone marrow cells", *Mutation Research*, 538, (2003), 101-107.
Posner, B. I., et al., "Peroxovanadium Compounds—A New Class of Potent Phosphotyrosine Phosphatase Inhibitors", *The Journal of Biological Chemistry*, 269(6), (1994), 4596-4604.
Reddy, P., et al., "Oocyte-Specific Deletion of Pten Causes Premature Activation of the Primordial", *Science*, 319, (Feb. 2008), 611-613.
Rosivatz, E., et al., "A Small-Molecule Inhibitor for Phosphatase and Tensin Homologue Deleted on Chromosome 10 (PTEN)", *ACS Chemical Biology*, 1(12), (2006), 780-790.
Schmid, A. C., et al., "Bisperoxovanadium compounds are potent PTEN inhibitors", *FEBS Letters*, 566, (2004), 35-38.
"International Application Serial No. PCT/SE2009/050049, International Preliminary Report on Patentability completed Apr. 9, 2010", 13 pgs.
"International Application Serial No. PCT/SE2009/050049, International Search Report mailed Apr. 17, 2009", 9 pgs.
"International Application Serial No. PCT/SE2009/050049, Written Opinion mailed Apr. 17, 2009", 11 pgs.
"Russian Application Serial No. 2010134371, Office Action dated Dec. 18, 2012", (English Translation), 3 pgs.
"Japanese Application Serial No. 2010-543036, Office Action mailed Jun. 25, 2013", (English Translation), 4 pgs.
"Australian Application Serial No. 2009205771, Examination Report mailed May 17, 2013", 5 pgs.
"European Application Serial No. 09702221.4, European Search Report mailed Apr. 8, 2011", 11 pgs.
Cummings, C., et al., "A Peroxovanadium Compound Induces Xenopus Oocyte Maturation: Inhibition by a Neutralizing Anti-insulin Receptor Antibody", Developmental Biology, 175(2), (1996), 338-346.

* cited by examiner

*Primary Examiner* — Misook Yu
*Assistant Examiner* — Kauser M Akhoon
(74) *Attorney, Agent, or Firm* — Schwegman Lundberg & Woessner, P.A.

(57) ABSTRACT

The invention relates to methods to be used in the maturation of ovarian follicles and oocytes. More specifically, the invention concerns the use of inhibitors of the phosphatase PTEN, such as oxovanadate and peroxovanadate complexes, in methods for in vitro and in vivo maturation of follicles and oocytes.

6 Claims, 3 Drawing Sheets

Control bpv (Hopic) 10uM

METHODS FOR IN VITRO MATURATION OF OVARIAN FOLLICLES

RELATED APPLICATIONS

This application is a U.S. National Stage Filing under 35 U.S.C. 371 from International Patent Application Serial No. PCT/SE2009/050049, filed Jan. 19, 2009, and published on Jul. 23, 2009 as WO 2009/091332 A1, which claims the priority benefit of U.S. Provisional Application Ser. No. 61/021,639, filed Jan. 17, 2008, and U.S. Provisional Application Ser. No. 61/024,210, filed Jan. 29, 2008, the contents of which are incorporated herein by reference in their entirety.

FIELD OF THE INVENTION

The invention relates to methods to be used in in vitro maturation of ovarian follicles and oocytes. More specifically the invention concerns the use of inhibitors of the phosphatase PTEN in methods for in vitro maturation of follicles and oocytes.

BACKGROUND

Inducing activation of ovarian follicles in order to achieve maturation is highly desirably from a research perspective but also within numerous fields of application. Primordial follicles could potentially serve as a source of oocytes for in vitro fertilization, but the ability to utilize activated and matured ovarian follicles for other applications, for instance post-chemotherapy or radiation treatment of cancer, is also of great importance. However, there is currently no means for primordial follicle activation, implying that a potentially vital source of oocyte material remains unexploited. In the light of the debate regarding in vitro fertilization, such considerations are increasingly important.

In clinics, if a woman's primordial follicles can not start to grow, i.e. to be activated from the dormant state, her follicles will not respond to hormones, such as follicle stimulating hormone (FSH). Therefore, the woman is infertile, and she can not use her own oocytes for in vitro fertilization. Currently, as abovementioned, there is no technique to use primordial follicles as sources of oocytes for in vitro fertilization. Thus, there is a need in the art to develop methods for inducing either in vivo and/or in vitro activation and maturation of ovarian follicles for various applications.

Prior art describes the lipid kinases phosphatidylinositol 3-kinases (PI3Ks), which phosphorylate the 3'-OH group on the inositol ring of inositol phospholipids. PTEN (phosphatase and tensin homolog deleted on chromosome ten), a lipid phosphatase, reverses this process and thus functions as a major negative regulator of PI3K action (Cantley, Science 2002, 296: 1655-1657.).

BRIEF DESCRIPTION OF THE INVENTION

The present inventors have identified PTEN as a factor that suppresses the activation of primordial follicles. In a mouse model with oocyte-specific deletion of the Pten gene, all primordial follicles were prematurely activated.

Accordingly, the present invention provides methods for the in vitro activation and maturation of ovarian follicles and oocytes comprising the use of one or more inhibitors of PTEN. The methods can be applied to activate follicles during in vitro maturation of follicles and oocytes for in vitro fertilization. The follicles can be non-growing follicles, such as primordial, intermediate and primary follicles.

The method can comprise incubating the follicles and/or oocytes in a physiologically acceptable medium comprising one or more inhibitors of PTEN. The medium can further comprise a gonadotropin such as FSH and/or CG.

The duration of the incubation can be any time that is sufficient to obtain activation and/or maturation of the ovarian follicles and/or oocytes.

The PTEN inhibitor can be present in any concentration providing activation and/or maturation of the ovarian follicles and/or oocytes, such as a concentration in the interval from 1 nM to 1.0 mM, especially from 1.0 to 100 µM.

In a preferred embodiment of the present invention, the activation and/or maturation of the ovarian follicles and/or oocytes comprises the following steps: (i) obtaining suitable cells and/or organs for activation and/or maturation of ovarian follicles and/or oocytes from a suitable subject, (ii) cultivating said cells and/or organs in a humidified incubator, e.g. at a temperature of substantially 37° C. and with approximately 5% $CO_2$, (iii) incubating the cells and/or organs either transiently or continuously with a PTEN inhibitor, in a concentration interval from 1 nM to 1.0 mM, preferably from 1.0 to 100 µM, in order to induce activation and/or maturation of said ovarian follicles and/or oocytes, and (iv) utilizing the obtained material according to the scope of the invention.

The methods according to the invention can be applied to human follicles, or follicles derived from an animal, such as a domestic or endangered animal. The domestic animal can e.g. be a horse, a cow, a pig, a cat, a dog.

The invention further provides use of one or more inhibitors of PTEN in the manufacture of a medicament for use in improving in vitro maturation of ovarian follicles and oocytes, specifically in vitro activation of non-growing follicles, such as primordial, intermediate and primary follicles.

The invention further provides a composition comprising one or more inhibitors of PTEN for enhancing the in vitro maturation of ovarian follicles and oocytes, specifically in vitro activation of non-growing follicles, such as primordial, intermediate and primary follicles. The composition can further comprise a pharmaceutically acceptable carrier, excipient or diluent.

Inhibitors of PTEN are described in WO 2005/097119 and corresponding U.S. application Ser. No. 10/599,748, WO 2004/075897 and the corresponding U.S. Ser. No. 10/546,632, which are all hereby incorporated by reference.

Inhibitors of PDZ-domain interactions, particular interactions between PDZ-domains in the PTEN associated MAGIs (membrane associated guanylate kinase proteins with inverse orientation) can be used as inhibitors of PTEN activity according to the invention. Such inhibitors are described in WO 2004/092346, U.S. Pat. No. 7,141,600, WO 2006/07542, which are all hereby incorporated by reference.

Peroxovanadium complexes have been shown to be potent inhibitors of PTEN (Schmid et al. FEBS Lett 2004, 566: 35-38; Rosivatz et al. ACS Chem Biol 2006, 1: 780-790).

Synthesis of peroxovanadium complexes can be performed as described by Shaver et al. (Inorg Chem 1993, 32:3109-3113), Rosivatz et al. (ACS Chem Biol 2006, 1: 780-790) and Posner et al. (J Biol Chem 1994, 269: 4596-604).

Examples of compounds which can be used according to the invention are;

bpV(bipy), Potassium Bisperoxo(bipyridine)oxovanadate (V), $K[VO(O_2)_2C_{10}H_8N_2]$.

bpV(phen), Potassium Bisperoxo(1,10-phenanthroline) oxovanadate (V), $K[VO(O_2)_2C_{12}H_8N_2]$ bpV(pic), Dipotassium Bisperoxo(picolinato)oxovanadate (V), $K_2[VO(O_2)_2C_6H_4NO_2]$.

bpV-HOpic Dipotassium Bisperoxo(5-hydroxypyridine-2-carboxyl)oxovanadate (V) $K_2[VO(O_2)_2C_6H_4NO_3]$.

VO-pic, Di-(picolinate) oxovanadate (IV), $VOC_{10}H_{10}NO_4$

VO-OHpic, Di-(3-hydroxypicolinate) oxovanadate (IV), $VOC_{10}H_{10}NO_6$ bpV-biguan, Potassium Bisperoxo(phenylbiguanide)oxovanadate (V), $K[VO(O_2)_2C_8H_{11}N_5]$ VO-biguan, Di-(phenylbiguanide)oxovanadate (IV), $VOC_{16}H_{20}N_{10}$ bpV-isoqu, Dipotassium Bisperoxo(isoquinolinecarboxylic acid)oxovanadate (V), $K_2[VO(O_2)_2C_{10}H_7NO_2]$;

compounds of the formula

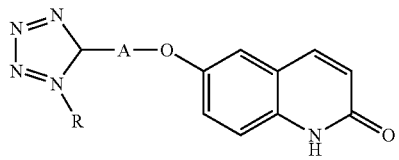

wherein

R is a cycloalkyl group,

A is a lower alkylene group, and the bond between 3- and 4-positions of the carbostyril nucleus means a single bond or a double bond;

an ascorbic acid derivative or dehydroascorbic acid derivative selected from the following:

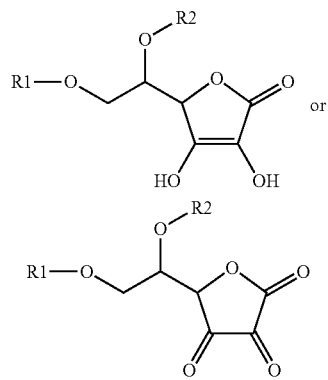

wherein,

R1 represents H, C1-C3 alkyl, aryl, alkylaryl, $(CH_2)_n COXR3$, $(CH_2)_n XCOR3$, $(CH_2)_n COR3$, $(CH_2)_n SO_2R3$, $(CH_2)_n XR3$, $(CH_2)_n SO_2XR3$, $(CH_2)_n XSO_2R3$, $(CH_2)_n NR3R4$, $(CH_2)_n CO(CH_2)_m XR3$;

R2 represents H, C1-C3 alkyl, aryl, alkylaryl, $(CH_2)_n COXR3$, $(CH_2)_n XCOR3$, $(CH_2)_n COR3$, $(CH_2)_n SO_2R3$, $(CH_2)_n XR3$, $(CH_2)_n SO_2XR3$, $(CH_2)_n XSO_2R3$, $(CH_2)_n NR3R4$, or $(CH_2)_n CO(CH_2)_m XR3$;

R3, R5, R6 independently are H, C1-C4 alkyl, aryl or alkylaryl;

R4 represents H, C1-C4 alkyl, aryl, alkylaryl, $NHSO_2R5$, $NHCO_2R5$, or NR5R6;

m=0 to 3; n=0 to 3; and X represents O or NR4;

compounds according to the formula

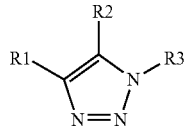

wherein,

R1 represents H, C1-C4 alkyl, aryl, alkylaryl, COXR2, COR2, $SO_2X$ R2, $SO_2R2$;

R2 represents H, C1-C4 alkyl, aryl, alkylaryl, $(CH_2)_n COX$ R4, $(CH_2)_n XCOR4$, $(CH_2)_n X$ R4, $(CH_2)_n SO_2X$ R4, $(CH_2)_n XSO_2R4$, $NHSO_2R4$, NHCOR4, $NHCO_2R4$, $NHCOCO_2R4$, or NR4R5;

R3 represents H, C1-C4 alkyl, aryl, alkylaryl, $(CH_2)_n COX$ R4, $(CH_2)_n XCOR4$, $(CH_2)_n X$ R4, $(CH_2)_n SO_2X$ R4, $(CH_2)_n XSO_2R4$, $NHSO_2R4$, NHCOR4, $NHCO_2R4$, $NHCOCO_2R4$, or NR4R5;

R4 represents H, C1-C4 alkyl, aryl, or alkylaryl;

R5 represents H, C1-C4 alkyl, aryl, alkylaryl, $NHSO_2R6$, NHCOR6, $NHCO_2R6$, NR6R7, or N=C(R6R7);

R6 represents H, C1-C4 alkyl, aryl, or alkylaryl;

R7 represents H, C1-C4 alkyl, aryl, or alkylaryl;

n=0 to 3; and X represents 0 Or NR5;

compounds according to the formula

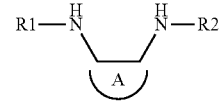

wherein,

A is a five or six member ring; R1 represents H, C1-C3 alkyl, aryl, alkylaryl, $(CH_2)_n COX$ R3, $(CH_2)_n XCOR3$, $(CH_2)_n COR3$, $(CH_2)_n SO_2R3$, $(CH_2)_n X$ R3, $(CH_2)_n SO_2X R3$, $(CH_2)_n XSO_2R3$, $NHSO_2R3$, $NHCO_2R3$, NHCOR3, $NHCOCO_2R3$, NR3R4, or $(CH_2)_n CO(CH_2)_m X3$;

R2 represents H, C1-C3 alkyl, aryl, alkylaryl, $(CH_2)_n COX$ R3, $(CH_2)_n XCOR3$, $(CH_2)_n COR3$, $(CH_2)_n SO_2R3$, $(CH_2)_n X$ R3, $(CH_2)_n SO_2X$ R3, $(CH_2)_n XSO_2R3$, $NHSO_2R3$, $NHCO_2R3$, NHCOR3, $NHCOCO_2R3$, NR3R4, or $(CH_2)_n CO(CH_2)_m X3$;

R3 represents H, C1-C4 alkyl, aryl, or alkylaryl;

R4 represents H, C1-C4 alkyl, aryl, alkylaryl, $NHSO_2R5$, $NHCO_2R5$, or NR5R6;

R5 represents H, C1-C4 alkyl, aryl, or alkylaryl;

R6 represents H, C1-C4 alkyl, aryl, or alkylaryl;

n=0-3; m=0-3; and X represents O, or NR4;

ring A may be saturated, unsaturated, or aromatic, and may optionally comprise N and O;

compounds according to the formula

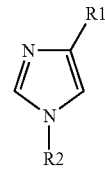

wherein,

R1 represents H, C1-C4 alkyl, aryl, alkylaryl, $(CH_2)_n COXR3$, $(CH_2)_m XCOR3$, $(CH_2)_m XR3$, $(CH_2)_n COR3$, $(CH_2)_n SO_2X$ R3, or $(CH_2)_m XSO_2R3$;

R2 represents H, C1-C4 alkyl, aryl, or alkylaryl;
R3 represents H, C1-C alkyl, aryl, or alkylaryl;
R4 represents H, C1-C4 alkyl, aryl, alkylaryl, NHSO₂R5, NHCO₂R5, N=C(R5R6), NR5R6;
R5 represents H, C1-C4 alkyl, aryl, or alkylaryl;
R6 represents H, C1-C4 alkyl, aryl, or alkylaryl;
m=1-3; n=0-3; and X represents O, or NR4;
substituted 1,10-phenanthroline-5,6-diones of the formula:

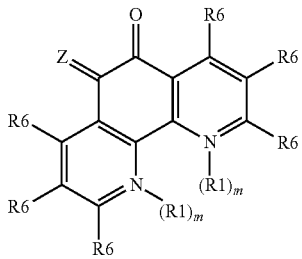

wherein,
R1 represents O, C1-C4 alkyl, $(CH_2)_n COXR2$, $(CH_2)_n X$-COR2, $(CH_2)_n XR2$, $(CH_2)_n COR2$, $(CH_2)_n SO_2 XR2$, $(CH_2)_n XSO_2 R2$, or $(CH_2)_n SO_2 R2$;
R2 represents H, C1-C4 alkyl, aryl, alkylaryl, NHSO₂R4, NHCOR4, NHCO₂R4, NHCOCO₂R4, or NR4R5;
R3 represents H, C1-C4 alkyl, aryl, alkylaryl, NHSO₂R4, NHCOR4, NHCO₂R4, NHCOCO₂R4, or NR4R5;
R4 represents H, C1-C4 alkyl, aryl, or alkylaryl;
R5 represents H, C1-C4 alkyl, aryl, or alkylaryl;
R6 at each occurrence is independently selected from hydrogen, halogen, NO₂, R4R10, C1-C4 $NH(CH_2)_p CO(CH_2)_q XR2$, $(CH_2)_p COXR2$, $(CH_2)_p XCOR2$, $(CH_2)_p XR2$, $(CH_2)_p COR2$, $(CH_2)_p SO_2 XR2$, or $(CH_2)_p XSO_2 R2$;
R7 represents H, C1-C4 alkyl, aryl, alkylaryl, SO₂R4, NHSO₂R4, NHCO₂R4, or NR8R9;
R8 represents independently H, C1-C4 alkyl, aryl, alkylaryl, $(CH_2)_n COXR2$, or $(CH_2)_n XR2$;
R9 represents independently H, C1-C4 alkyl, aryl, alkylaryl, $(CH_2)_n COXR2$, $(CH_2)_n XR2$, $(CH_2)_p COXR2$, $(CH_2)_p XCOR2$, $(CH_2)_p X R2$, $(CH_2)_p COR2$, $(CH_2)_p SO_2 X R2$, $(CH_2)_p XSO_2 R2$, or $(CH_2)_p SO_2 R2$;
R10 represents H, C1-C4 alkyl, aryl, alkylaryl, SO₂R4, NHSO₂R4, NHCO₂R4, or NR8R9;
m represents independently 0 or 1; n=1-5; p=0-5; q=0-5; X represents O or NR3; and Z represents O or NR7;
substituted phenanthrene-9,10-diones of the formula:

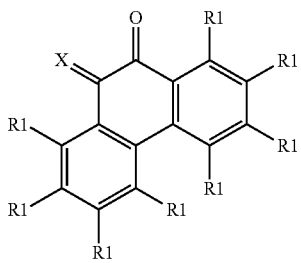

wherein,
R1 represents H, NO₂, NR5R6, halogen, cyano, alkyl, alkylaryl, carbonyl, carboxy, COR2, or CONR5R6;
R2 and R3 represent independently H, C1-C4 alkyl, aryl, or alkylaryl;

R4 represents H, C1-C4 alkyl, aryl, alkylaryl, SO₂R2, NHSO₂R2, NHCOR2, NHCO₂R2, N=CR2R3, or NR5R6;
R5 represents H, C1-C4 alkyl, aryl, alkylaryl, $(CH_2)_n COXR2$, $(CH_2)_n X R2$, $(CH_2)_n CO(CH_2)_m X R2$, SO₂R2, $(CH_2)_n CO(CH_2)_n COXR2$, or $(CH_2)_n COR2$;
R6 represents H, C1-C4 alkyl, aryl, alkylaryl, $(CH_2)_n COXR2$, $(CH_2)_n X R2$, $(CH_2)_n CO(CH_2)_m X R2$, SO₂R2, $(CH_2)_n CO(CH_2)_n COXR2$, or $(CH_2)_n COR2$;
m=0-3; n=0-3; and X represents CR2R3, O, or NR4;
compounds of the formula:

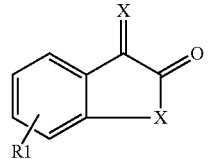

wherein,
R1 represents H, NO₂, NR5R6, halogen, cyano, alkyl, alkylaryl, carbonyl, carboxy, COR2, CONR5R6, SO₃R2, or SO₂NR2R3;
R2 and R3 represent independently H, C1-C4 alkyl, aryl, or alkylaryl;
R4 represents H, C1-C4 alkyl, aryl, alkylaryl, SO₂R2, NHSO₂R2, NHCOR2, NHCO₂R2, N=CR2R3, or NR5R6;
R5 represents H, C1-C4 alkyl, aryl, alkylaryl, $(CH_2)_n COXR2$, $(CH_2)_n XR2$, $(CH_2)_n CO(CH_2)_m X R2$, SO₂R2, $(CH_2)_n CO(CH_2)_n COXR2$, or $(CH_2)_n COR2$;
R6 represents H, C1-C4 alkyl, aryl, alkylaryl, $(CH_2)_n COXR2$, $(CH_2)_n XR2$, $(CH_2)_n CO(CH_2)_m X R2$, SO₂R2, $(CH_2)_n CO(CH_2)_n COXR2$, or $(CH_2)_n COR2$;
m=0-3; n=0-3; and X represents CR2R3, O, or NR4.
substituted phenanthren-9-ols of the formula:

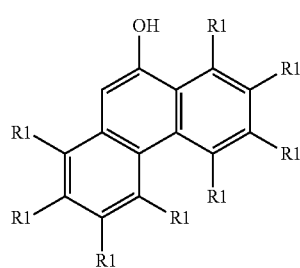

wherein,
R1 represents H, NO₂, NR5R6, halogen, cyano, alkyl, alkylaryl, carbonyl, carboxy, COR2, or CONR5R6;
R2 and R3 represent independently H, C1-C4 alkyl, aryl, or alkylaryl;
R4 represents H, C1-C4 alkyl, aryl, alkylaryl, SO₂R2, NHSO₂R2, NHCOR2, NHCO₂R2, N=CR2R3, or NR5R6;
R5 represents H, C1-C4 alkyl, aryl, alkylaryl, $(CH_2)_n COXR2$, $(CH_2)_n XR2$, $(CH_2)_n CO(CH_2)_m X R2$, SO₂R2, $(CH_2)_n CO(CH_2)_n COXR2$, or $(CH_2)_n COR2$;
R6 represents H, C1-C4 alkyl, aryl, alkylaryl, $(CH_2)_n COXR2$, $(CH_2)_n XR2$, $(CH_2)_n CO(CH_2)_m X R2$, SO₂R2, $(CH_2)_n CO(CH_2)_n COXR2$, or $(CH_2)_n COR2$;
m=0-3; n=0-3; and X represents CR2R3, O, or NR4;

substituted naphthalene-1,2-diones of the formula:

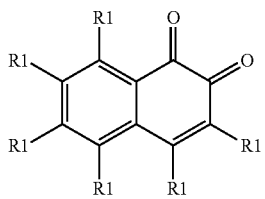

wherein,

R1 represents H, NO$_2$, NR3R4, halogen, cyano, alkyl, alkylaryl, carbonyl, carboxy, (CH$_2$)$_n$COXR3, COR2, SO$_3$R2, SO$_2$NR3R4, NHSO$_2$R3, NHCO$_2$R3, NHCOR3, NHCOCO$_2$R3, NR3R4, or CONR3R4;

R2 represents H, C1-C4 alkyl, aryl, or alkylaryl;

R3 and R4 represent independently H, C1-C4 alkyl, aryl, alkylaryl, (CH$_2$)$_n$COXR2, (CH$_2$)$_n$OR2, or (CH$_2$)$_n$CO(CH$_2$)$_m$AR2;

m=0-3; n=0-3; and X represents O, or NR2;

substituted naphthalene-1,4-diones of the formula:

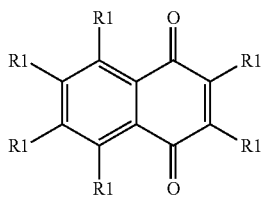

wherein

R1 represents H, NO$_2$, NR3R4, halogen, cyano, alkyl, alkylaryl, carbonyl, carboxy, (CH$_2$)$_n$COXR3, COR2, SO$_3$R2, SO$_2$NR3R4, NHSO$_2$R3, NHCO$_2$R3, NHCOR3, NHCOCO$_2$R3, NR3R4, or CONR3R4;

R2 represents H, C1-C4 alkyl, aryl, or alkylaryl;

R3 and R4 represent independently H, C1-C4 alkyl, aryl, alkylaryl, (CH$_2$)$_n$COXR2, (CH$_2$)$_n$OR2, or (CH2)$_n$CO(CH$_2$)$_m$XR2, m=0-3; n=0-3; and X represents O, or NR2; and compounds having the formula

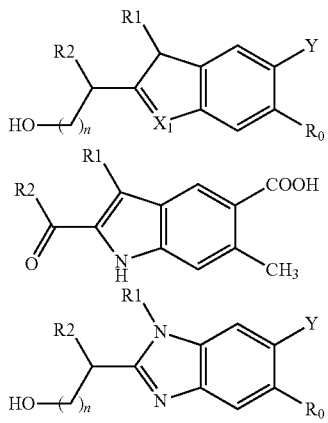

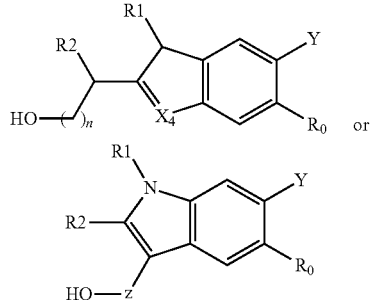

wherein n is 0, 1 or 2;

X1 is NH, N(CH$_3$), CH$_2$, CH(CH$_3$), C(CH$_3$)$_2$, O, S, S(O), or SO$_2$;

R0 is selected from the group consisting of C1-C3 alkyl, cyclopropyl, halo, OR5 and S(O)$_m$R5 in which m is 0, 1 or 2;

R1 and R2 are independently selected from the group consisting of C2-C8 alkenyl, phenylcyclopropyl, phenylpropenyl, R6-X2-C(R8)(R8)-R7-, R6-X2-N(R8)-R7-, and R10X3R7-;

R3 and R4 are independently hydrogen, methyl or ethyl;

R5 is methyl or ethyl;

R6 is selected from the group consisting of hydrogen, C1-C10 alkyl, aryl, W, Y, NH$_2$, NHCONR3R4, NHCOOR3 and NHSO$_2$R9;

R7 is selected from the group consisting of a direct bond, an alkyl group having from 1 to 10 carbon atoms, aryl, —(NH)$_p$(CH$_2$CH$_2$O)$_q$(NH)$_p$— in which p is 0 or 1 and q is an integer from 1 to 4, and W;

R8 is selected from the group consisting of H, Y, OH, —NHCONR3R4; —NHCOOR3; —NHSO$_2$R9, —(CH$_2$)$_r$CO$_2$R3, and (CH$_2$)$_r$CONR3R4 in which r is an integer from 1 to 3;

R9 is aryl C1-C6 alkyl;

R10 is selected from C1-C10 alkyl, aryl and W;

X2 is selected from the group consisting of a direct bond, —NH—, —N(CH$_3$)—, —NCONR3R4, —NCOOR3, and —NSO$_2$R9;

X3 is selected from O, S, SO and SO$_2$;

X4 is selected from —CH—, C-halogen, —C(CH$_3$) or —C(C$_2$H$_5$);

W is a saturated carbocyclic or heterocyclic group;

Y is selected from the group consisting of COOH, COOR3, CONR3R4, CONHSO$_2$R5, hydroxymethyl, —CH$_2$COOH, CH$_2$CONR3R4; and 5-tetrazolyl;

Z is —CH$_2$—, —CH(CH$_3$)—, —C(CH$_3$)$_2$— or —CO—;

Anti-sense oligonucleotides, and doubled stranded RNA targeted to nucleic acids encoding PTEN can be used as inhibitors of PTEN according to the invention. Such compounds are described in WO 01/07457 and WO 01/90341, WO 2004/27030 and WO 2004/63329 and the corresponding U.S. Pat. Nos. 6,020,199 and 6,284,538, which are all hereby incorporated by reference. Antibodies and/or antibody fragments acting as inhibitors specific for PTEN are also within the scope of the present invention.

The invention further provides methods for the identification of compounds that potentially can be used for in vitro activation of primordial follicles. The method comprises measurement of the ability of the compound to act as an inhibitor of PTEN activity.

PTEN activity can be measured as phosphate release as described by Schmid et al (FEBS Lett 2004, 566: 35-38). Essentially, enzyme activity of recombinant PTEN is measured in 200 mM Tris, pH 7.4, containing 50 ng/μl BSA, 150 μM synthetic dipalmitoyl-PtdIns(3,4,5)P3 (Cell Signals) and 0.25% (w/v) octyl glycoside (Sigma) at 30° C. for 30 min. In order to stop the enzyme reaction, 0.7 vol of colour reagent (2.3 mg/ml malachite green in 3.6 M 17 HCl and 17 mM ammonium molybdate) is added to the assay. The mixture is allowed to develop for 20 min and the absorbance at 625 nm is measured.

A compound is defined as an inhibitor of PTEN if the compound has an IC50 of less than 100 μM, preferably an IC50 of less than 10 μM, or even more preferably an IC50 of less than 1 μM.

Function of the PTEN inhibitor can be verified by measurement of increased PI3 kinase activity in the presence of PTEN, PI3 kinase activity can also be measured by the phosphorylation level of Akt at serine 473.

The invention further provides methods for the in vitro maturation of an oocyte which comprises the activation of primordial follicles according to the methods of the invention.

The invention also provides methods of in vitro fertilization comprising implanting an embryo in need thereof, wherein said embryo is produced by a method comprising treating a mature oocyte with sperm, wherein said oocyte is produced by a method which comprises the activation of primordial follicles according to the methods of the invention.

The invention further provides methods for improving embryo development after in vitro fertilization or embryo transfer in a female mammal comprising implanting into the female mammal an embryo derived from an oocyte, wherein said oocyte is produced by a method which comprises the activation of primordial follicles according to the methods of the invention.

The invention further provides methods for the in vivo activation and maturation of ovarian follicles and oocytes comprising administration of a composition comprising one or more inhibitors of PTEN. Preferably, the administration is made by local injection, more preferably by intrafollicular or intrabursal injection. The follicles can be non-growing follicles, such as primordial, intermediate and primary follicles. The methods can be applied to humans or animals, such as domestic or endangered animals. The domestic animal can e.g. be a horse, a cow, a pig, a cat, a dog.

The local injection can be made with the aid of laparoscopy or ultrasound.

The invention further provides use of one or more inhibitors of PTEN in the manufacture of a pharmaceutical composition for use in in vivo activation and maturation of ovarian follicles and oocytes by, specifically in vivo activation of non-growing follicles, such as primordial, intermediate and primary follicles. The composition can be intended to be administered by local injection or other types of local delivery, preferably by intrafollicular or intrabursal injection. The composition can be intended for human or veterinary use.

The invention further provides a composition comprising one or more inhibitors of PTEN for use in in vivo activation and maturation of ovarian follicles and oocytes, specifically in vivo activation of non-growing follicles, such as primordial, intermediate and primary follicles. The composition can further comprise a pharmaceutically acceptable carrier, excipient or diluent. The composition can be formulated for local injection, preferably for intrafollicular or intrabursal injection. The composition can be intended for human or veterinary use.

Ovaries from 35-day-old mice were embedded in paraffin and sections of 8-μm thickness were prepared and stained with hematoxylin. A. Control mice: In control normal mice, there are primordial follicles (arrow in the inset). B-C. Mice lacking PTEN in oocytes. In oocytes that lack PTEN, all follicles grow up prematurely (C, arrows), and the whole ovary is much bigger (B).

Figure 2:
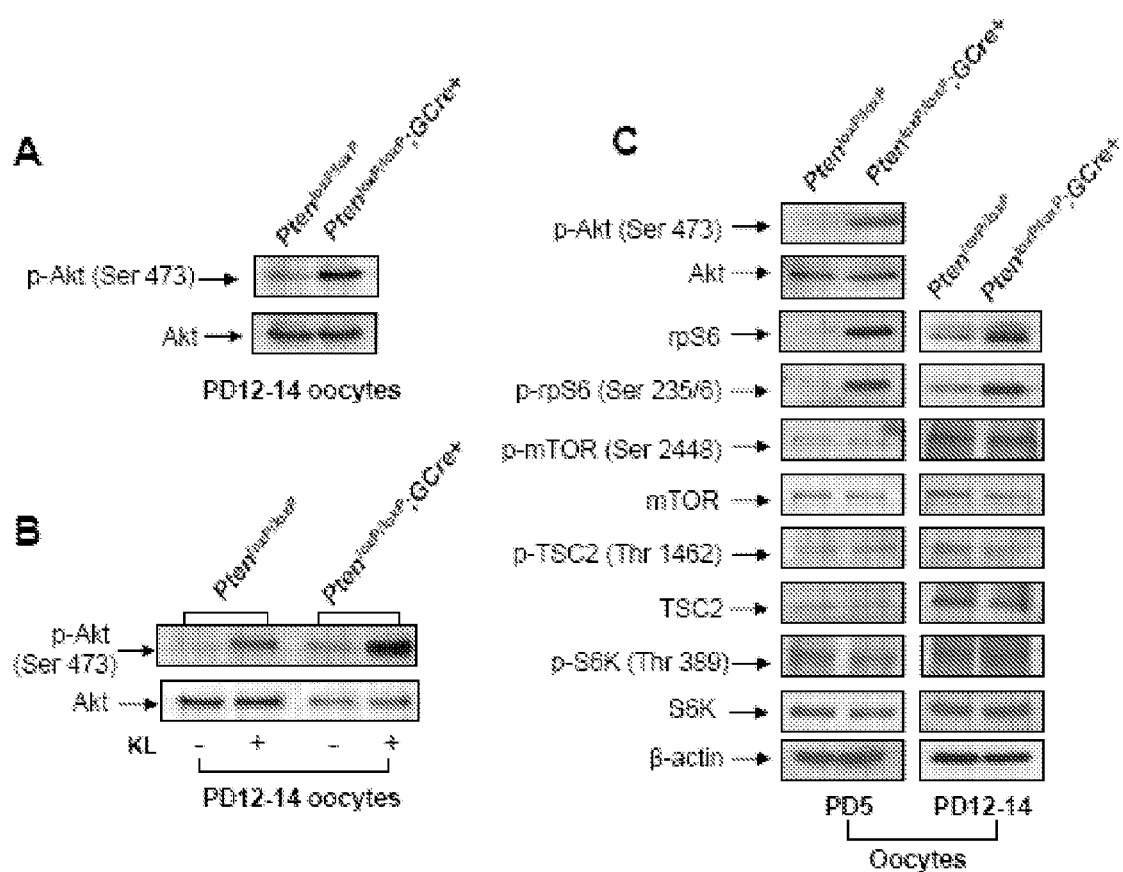

FIG. 2. Enhanced Akt Signaling in $Pten^{loxP/loxP}$; GCre+ Oocytes.

Oocytes were isolated from ovaries of $Pten^{loxP/loxP}$; GCre+ and $Pten^{loxP/loxP}$ mice at PD5 and PD12-14, and western blots were performed (A) Levels of p-Akt (serine 473) and total Akt in PD12-14 $Pten^{loxP/loxP}$; GCre+ and $Pten^{loxP/loxP}$ oocytes. (B) Activation of Akt (p-Akt, serine 473) by Kit ligand (KL) treatment (100 ng/ml, 2 min) in PD12-14 $Pten^{loxP/loxP}$; GCre+ and $Pten^{loxP/loxP}$ oocytes. Levels of Akt were used as internal controls. (C) Signaling studies in $Pten^{loxP/loxP}$; GCre+ and $Pten^{loxP/loxP}$ oocytes at PD5 and PD12-14, showing levels of p-Akt (serine 473), rpS6, p-rpS6 (serine 235/6), p-mTOR (serine 2448), p-TSC2 (threonine 1462), and p-S6K (threonine 389). Levels of total Akt, mTOR, TSC2, S6K, and β-actin were used as internal controls. All experiments were repeated at least 3 times. For isolation of PD5 oocytes for western blot, 10-15 $Pten^{loxP/loxP}$; GCre+ or $Pten^{loxP/loxP}$ mice were used for each lane. For isolation of PD12-14 oocytes, 3-5 $Pten^{loxP/loxP}$; GCre+ mice or 6-10 $Pten^{loxP/loxP}$ mice were used per lane. In each lane, 30-40 μg of protein sample was loaded.

Figure 3:
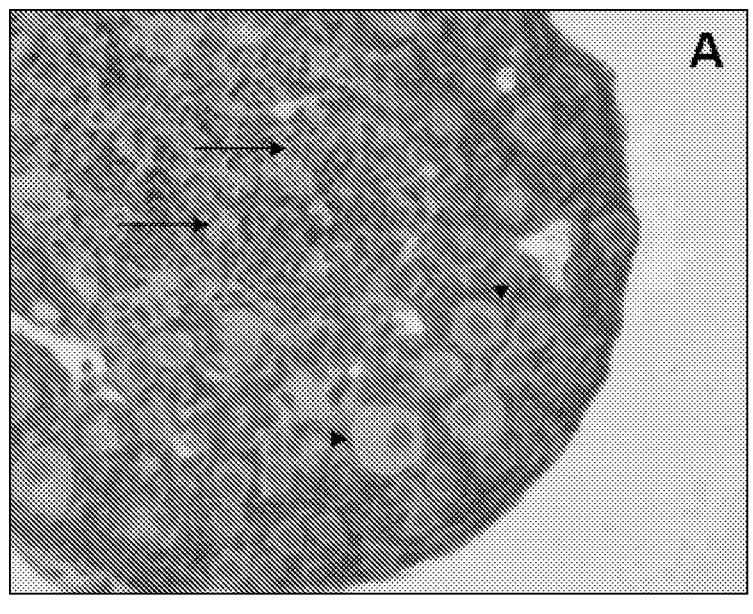
Figure 3:
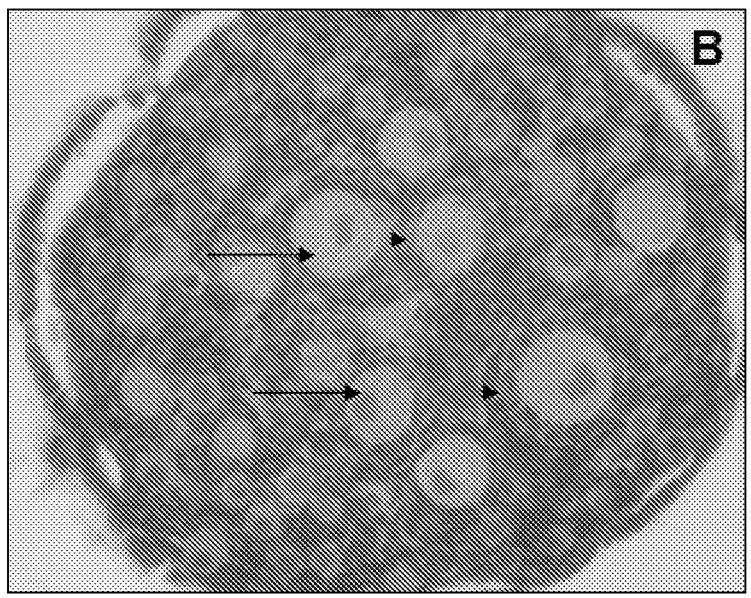

FIG. 3. PTEN Inhibitor Promotes the Survival and Development of Primordial Follicles in Cultured Mouse Ovaries.

Postnatal day 4 mouse ovaries containing primordial follicles were cultured for 8 days with carrier (A) or PTEN inhibitor bpv (Hopic) (B). The PTEN inhibitor enhances the survival rate of follicles in the cultured ovaries (arrows in B vs. arrows in A, indicating rescued necrosis in PTEN inhibitor treated ovaries); also the PTEN inhibitor stimulates the proliferation and differentiation of flattened pre-granulosa cells (arrowheads, A) into cuboidal granulosa cells (arrowheads, B), which is an essential step for the activation of primordial follicles into the growing stage

DETAILED DESCRIPTION OF THE INVENTION

Currently, if the animal or human primordial follicles are cultured in vitro, it is very difficult for them to initiate their growth, and undergo maturation. According to the present invention, in the presence of PTEN inhibitors, primordial follicles from human or domestic/endangered animals can be activated in vitro, i.e. the growth of primordial follicles will be initiated. These activated follicles can then be cultured further, till they mature, which can be used for in vitro fertilization.

The method is to culture slices of ovaries containing primordial follicles from human or domestic/endangered animals, with temporary treatment with one or more PTEN inhibitors, to initiate their growth. Once the growth of follicles is induced, PTEN inhibitors will be withdrawn, further follicular culture will be maintained routinely with current available techniques.

This method is useful to women whose primordial follicles can not be naturally activated, or in women who will go through a chemotherapy or radiation therapy for cancers. This method can also be used to in vitro activate primordial follicles of domestic or endangered animals for enhancing the follicle recourses as well as the rate of successful in vitro fertilization.

The effective suppression of PTEN activity in the cultured ovarian slices can be monitored using slices of mouse ovaries that are cultured at the same time.

EXAMPLES

Example 1

Figure 1:
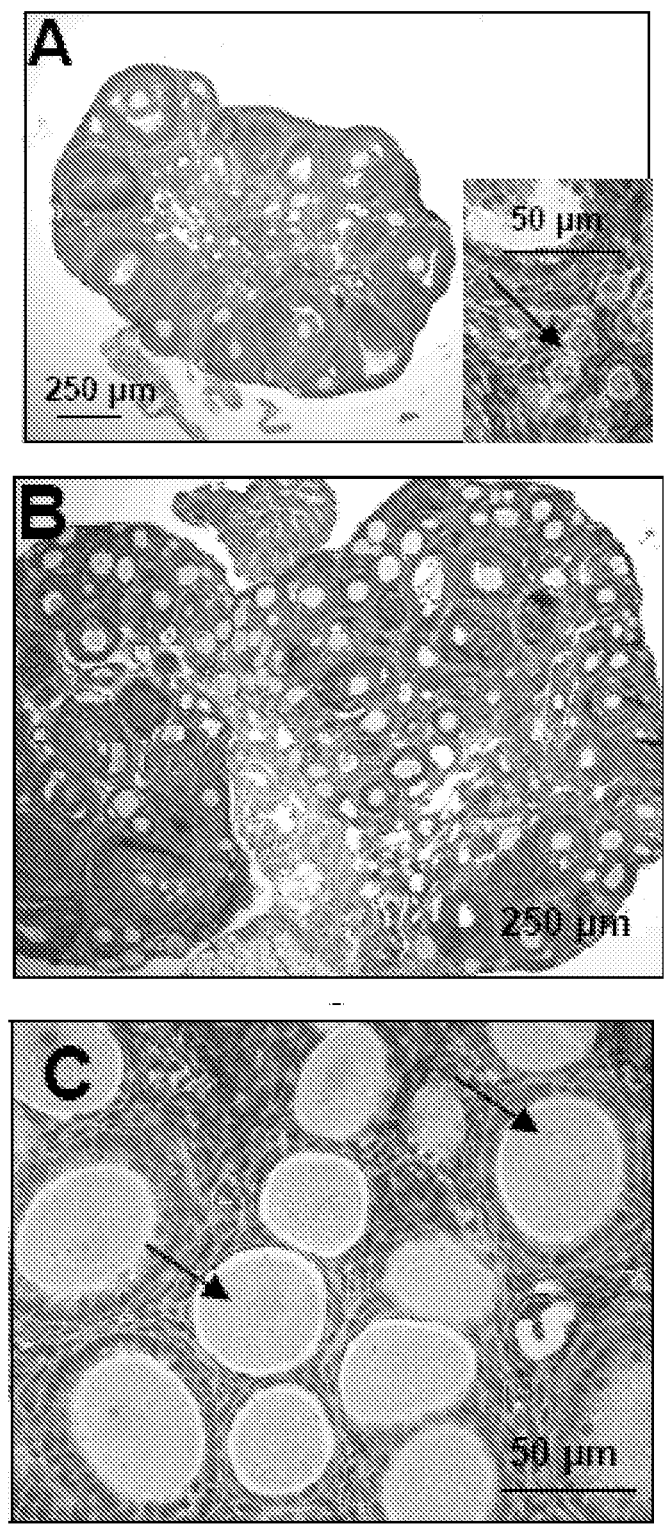
FIG. 1. Overactivation of Primordial Follicles in Mice Lacking PTEN from their Oocytes.

Functional Roles of the Oocyte PI3K Pathway in Mammalian Follicular Activation To study the functional roles of the oocyte PI3K pathway in mammalian follicular activation, the Pten gene was deleted from mouse oocytes by crossing $Pten^{loxP/loxP}$ mice (Groszer et al., Science 2001, 294: 2186) with transgenic mice expressing growth differentiation factor 9 (Gdf-9) promoter-mediated Cre recombinase (referred to as GCre mice), which is active specifically in oocytes (Lan et al. Biol. Reprod. 2004, 71: 1469). It was found that during a testing period from 6 to 34 weeks of age, the $Pten^{loxP/loxP}$; GCre+ females, i.e. mice lacking PTEN from their oocytes, produced a maximum of one litter but became infertile in early adulthood (i.e. after 12-13 weeks of age). To study how the loss of Pten from oocytes impedes mouse fertility, we compared the first wave of postnatal follicular development in $Pten^{loxP/loxP}$; GCre+ and control ($Pten^{loxP/loxP}$) mice. No apparent morphological difference in postnatal day (PD) 5 ovaries of $Pten^{loxP/loxP}$; GCre+ and control mice were found. The ovaries of both genotypes had mostly primordial follicles containing small oocytes surrounded by flattened pre-granulosa cells, and some activated follicles containing enlarged oocytes, with comparable numbers. By PD 35, the $Pten^{loxP/loxP}$; GCre+ ovaries (FIG. 1, B) remained larger than control ovaries and contained significantly more activated follicles (FIG. 1, C) Virtually no primordial follicles could be identified in mutant ovaries whereas a majority of the follicles in control ovaries were still at the primordial stage. Therefore, the entire pool of primordial follicles had been activated in $Pten^{loxP/loxP}$; GCre+ ovaries.

Thus, activation of the pool of primordial follicles ends up with follicle depletion. This causes POF (premature ovarian failure) in $Pten^{loxP/loxP}$; GCr+ mice. The phenotype observed in these mice resembles that of human POF (Beck-Peccoz and Persani, Orphanet. J. Rare. Dis. 2006, 1: 9). To elucidate the molecular mechanisms underlying the accelerated oocyte enlargement in $Pten^{loxP/loxP}$; GCre+ ovaries, Akt signaling in oocytes isolated from ovaries of PD12-14 $Pten^{loxP/loxP}$; GCre+ and control mice was studied. It was found that the level of phospho-Akt (p-Akt, serine 473) was elevated in $Pten^{loxP/loxP}$; GCre+ oocytes that were cultured in vitro and starved of serum (FIG. 2A). In addition, Kit ligand (KL), which can activate the PI3K pathway in growing oocytes through its oocyte surface receptor Kit (Reddy et al. Dev. Biol. 2005, 281: 160), activated Akt to a greater extent in $Pten^{loxP/loxP}$; GCre+ oocytes than in control oocytes (FIG. 2 2B). Thus, the loss of Pten in oocytes leads to enhanced oocyte PI3K/Akt signaling. In order to investigate the cause of accelerated oocyte growth in $Pten^{loxP/loxP}$; GCre+ ovaries, it was studied whether the enhanced PI3K/Akt signaling led to increased activation of ribosomal protein S6 (rpS6). At PD5, a developmental stage with no apparent morphological differences between $Pten^{loxP/loxP}$; GCre+ and control ovaries (FIG. 2, A-C), the activation of Akt had already been elevated in $Pten^{loxP/loxP}$; GCre+ oocytes (FIG. 2C, PD5, p-Akt). This correlated with enhanced expression (FIG. 2C, PD5, rpS6) and phosphorylation (indicating activation) of rpS6 (FIG. 2C, PD5, p-rpS6, serine 235/6). This result suggests that enhanced protein translation had already started when the Gdf-9-Cre-mediated Pten deletion in oocytes had just taken place. Similarly, in oocytes isolated from $Pten^{loxP/loxP}$; GCre+ ovaries at PD12-14, enhanced PI3K/Akt signaling led to elevation of both expression and phosphorylation of rpS6 (FIG. 2C, PD12-14). However, activation of the mammalian target of rapamycin (mTOR)-p70 S6 kinase (S6K) cascade was not increased by loss of Pten, as the levels of phospho-mTOR (p-mTOR, serine 2448), phospho-tuberin/TSC2 (p-TSC2, threonine 1462), and phospho-S6K (p-S6K, threonine 389) at PD5 and PD12-14 remained similar in $Pten^{loxP/loxP}$; GCre+ and control oocytes (FIG. 2C). Thus, the enhanced activation of rpS6 was caused by elevated rpS6 expression per se (FIG. 2C). However, the phosphorylation of rpS6 and S6K in mutant oocytes was sensitive to the PI3K-specific inhibitor LY294002 and the mTOR-specific inhibitor rapamycin, indicating that activation of rpS6 in $Pten^{loxP/loxP}$; GCre+ oocytes is dependent on the activities of PI3K and mTOR. It has previously been hypothesized that unknown intra-ovarian factors stimulate some primordial follicles to initiate growth while the rest of the follicles remain quiescent.

Example 2

PTEN Inhibitor Promotes the Survival and Development of Primordial Follicles in Cultured Mouse Ovaries Postnatal day 4 mouse ovaries were removed aseptically and the whole ovary was cultured in a Cell Strainer (40 μm pore size) (BD Biosciences, Stockholm, Sweden) in 1 ml alpha-MEM medium (Gibco-BRL) supplemented with 28 mM ascorbic acid and 0.3% (w/v) BSA, with or without 10 μM of the PTEN inhibitor bpV-HOpic (Dipotassium Bisperoxo(5-hydroxypyridine-2-carboxyl)oxovanadate (V), $K_2[VO(O_2)_2C_6H_4NO_3]$). The cultured ovaries were incubated in a humidified incubator (5% $CO_2$, 37° C.) with one-third of the medium exchanged for fresh medium every day for the duration of the culture period. For fixation, the ovaries were washed once in PBS and fixed overnight in 4% paraformaldehyde, and embedded for morphological analysis.

The PTEN inhibitor enhances the survival rate of follicles in the cultured ovaries (arrows in FIG. 3B vs. arrows in FIG. 3A) indicating rescued necrosis in PTEN inhibitor treated ovaries. Also the PTEN inhibitor stimulates the proliferation and differentiation of flattened pre-granulosa cells (arrowheads, FIG. 3A) into cuboidal granulosa cells (arrowheads, FIG. 3B), which is an essential step for the activation of primordial follicles into the growing stage.

CONCLUSIONS

The present data demonstrate that the oocyte PTEN functions as a suppressor of follicular activation. The intra-oocyte PTEN/PI3K signaling cascade appears to play a role in the initiation of oocyte growth. We propose that activation of the PI3K pathway in each individual oocyte may be essential in determining the fate of the primordial follicle—whether it remains dormant, whether it becomes activated at a certain time, or whether it undergoes atresia directly from the primordial stage. Furthermore, a distinctive ovarian phenotype of POF in mice with oocyte-specific ablation of Pten is demonstrated, which is caused by excessive activation and depletion of primordial follicles. Thus, the findings of this study have broad physiological and clinical implications, contributing to in-depth understandings of both normal ovarian physiology and the development of ovarian diseases. In humans, POF is defined as a primary ovarian defect characterized by absent menarche (primary amenorrhea) or premature depletion of ovarian follicles/arrested folliculogenesis before the age of 40 years (secondary amenorrhea), with an estimated incidence of 1% (Beck-Peccoz and Persani, Orphanet. J. Rare. Dis. 2006, 1: 9). Among various possible causes of POF, genetic variations leading to overactivation and depletion of follicles may be one of them in humans. On the other hand, the retardation of follicle activation and/or excessive primordial follicle atresia, both of which may be caused by underactivation of the PI3K pathway in oocytes, can also lead to POF, albeit from opposite directions. Recognition of the importance of PTEN/PI3K signaling network in oocytes opens up new prospects for the understanding of the physiological and pathological processes of the mammalian ovary.

The invention claimed is:

1. A method for the in vitro activation of mammalian non-growing follicles, the method comprising the step of incubating the mammalian follicles in a physiological acceptable medium comprising one or more inhibitors of PTEN, wherein the inhibitor of PTEN is selected from:

Bisperoxo(bipyridine)oxovanadate,
Bisperoxo(1,10-phenanthroline)oxovanadate,
Bisperoxo(picolinato)oxovanadate,
Bisperoxo(5-hydroxypyridine-2-carboxyl)oxovanadate,
Di-(picolinate) oxovanadate,
Di-(3-hydroxypicolinate) oxovanadate,
Bisperoxo(phenylbiguanide)oxovanadate,
Di-(phenylbiguanide)oxovanadate, or
Bisperoxo(isoquinolinecarboxylic acid)oxovanadate.

2. The method according to claim 1, wherein the non-growing follicles, are selected from primordial, intermediate and primary follicles.

3. The method according to claim 1, wherein the activated follicles are further used for in vitro fertilization.

4. The method according to claim 1, wherein the non-growing follicles are human.

5. A method for the in vitro maturation of an oocyte which comprises the activation of non-growing follicles according to claim 1.

6. A method of in vitro fertilization comprising implanting an embryo, wherein said embryo is produced by a method comprising treating a mature oocyte with sperm, wherein said oocyte is produced by the method of claim 5.

* * * * *